(12) United States Patent
Fan et al.

(10) Patent No.: US 12,116,342 B2
(45) Date of Patent: Oct. 15, 2024

(54) METHOD FOR PREPARING BRIVARACETAM AND INTERMEDIATE THEREOF

(71) Applicants: ZHEJIANG HUAHAI PHARMACEUTICAL CO., LTD, Zhejiang (CN); SHANGHAI SYNCORES TECHNOLOGIES INC. LTD., Shanghai (CN)

(72) Inventors: Haisheng Fan, Shanghai (CN); Yipeng Zhan, Shanghai (CN); Kai Yin, Shanghai (CN); Xiang Ji, Shanghai (CN); Fenghao Liu, Shanghai (CN); Kaiqiang Shi, Shanghai (CN); Xiaowen Guo, Shanghai (CN); Luning Huang, Shanghai (CN); Anping Tao, Shanghai (CN); Jianguo An, Shanghai (CN); Hong Gu, Shanghai (CN)

(73) Assignees: ZHEJIANG HUAHAI PHARMACEUTICAL CO., LTD, Zhejiang (CN); SHANGHAI SYNCORES TECHNOLOGIES INC. LTD., Shanghai (CN)

( * ) Notice: Subject to any disclaimer, the term of this patent is extended or adjusted under 35 U.S.C. 154(b) by 765 days.

(21) Appl. No.: 17/312,195

(22) PCT Filed: Dec. 12, 2019

(86) PCT No.: PCT/CN2019/124801
§ 371 (c)(1),
(2) Date: Jun. 9, 2021

(87) PCT Pub. No.: WO2020/125536
PCT Pub. Date: Jun. 25, 2020

(65) Prior Publication Data
US 2022/0048856 A1  Feb. 17, 2022

(30) Foreign Application Priority Data
Dec. 19, 2018 (CN) .......................... 201811558017.3

(51) Int. Cl.
*C07D 207/27* (2006.01)
(52) U.S. Cl.
CPC ........ *C07D 207/27* (2013.01); *C07B 2200/07* (2013.01); *C07B 2200/13* (2013.01)
(58) Field of Classification Search
CPC .......................... C07D 207/27; C07B 2200/07
See application file for complete search history.

(56) References Cited

U.S. PATENT DOCUMENTS

2006/0020022 A1* 1/2006 Chekal .................... A61P 43/00
549/403
2019/0119206 A1   4/2019 Defrance et al.

FOREIGN PATENT DOCUMENTS

CN  106748950 A   5/2017
CN  107513031 A   12/2017
(Continued)

OTHER PUBLICATIONS

Google English Machine Translation of CN 106748950, pub. May 31, 2017, p. 1-10. (Year: 2107).*
(Continued)

*Primary Examiner* — Kamal A Saeed
*Assistant Examiner* — Karen Cheng
(74) *Attorney, Agent, or Firm* — Renner, Otto, Boisselle & Sklar, LLP

(57) ABSTRACT

The present application relates to a method (I) for preparing a brivaracetam intermediate, comprising the steps of dissolving the compound represented by B-P and 1S,2S-diphenylethylenediamine in a solvent for resolution, crystallizing, filtering, and recrystallizing to obtain the compound represented by B-Q, which is then converted to the brivaracetam intermediate represented by B-R. This method can effectively resolve the compound represented by B-P. The present application also provides a method for preparing brivaracetam using the compound represented by B-R. The method can separate the effective components only through simple steps such as extraction, washing, drying, and concentration without requiring use of chiral chromatography column to separate isomers in the preparation process, and thus the separation process is simple, greatly reducing the production cost of brivaracetam.

(Continued)

-continued

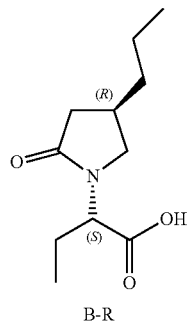

B-R

18 Claims, 3 Drawing Sheets

(56) References Cited

FOREIGN PATENT DOCUMENTS

| CN | 108101823 A | 6/2018 |
|---|---|---|
| CN | 108101824 A | 6/2018 |
| EP | 1 806 339 A1 | 7/2007 |
| JP | 2004182670 A | 7/2004 |
| WO | 2005/028435 A1 | 3/2005 |
| WO | 2007/065634 A1 | 6/2007 |
| WO | 2017/076738 A1 | 5/2017 |
| WO | 2018042393 A1 | 3/2018 |

OTHER PUBLICATIONS

Supplementary European Search Report issued for corresponding EP Application No. 19901084.4, mailed Oct. 26, 2021.
Original and English Translation of the First Chinese Office Action issued for corresponding Chinese Application No. 201980070829.X, mailed Jul. 4, 2022.
Leo A. Paquette, "Chiral Reagents for Asymmetric Synthesis," Dec. 31, 2019, translation from the English language edition published by John Wiley & Sons, Inc.
Original and English Translation of the International Search Report for corresponding International Patent Application No. PCT/CN2019/124801, dated Feb. 20, 2020.
Original of the First Chinese Office Action issued for priority Chinese Application No. 201811558017.2, mailed Aug. 10, 2023.

* cited by examiner

METHOD FOR PREPARING BRIVARACETAM AND INTERMEDIATE THEREOF

This application is a national phase of International Application No. PCT/CN2019/124801 filed Dec. 12, 2019, which claims priority of Chinese Patent Application No. 201811558017.3, filed Dec. 19, 2018, all of which are incorporated herein by reference.

FIELD OF THE INVENTION

The present application relates to the field of medical technology, particularly to a method for preparing brivaracetam and intermediate thereof.

BACKGROUND OF THE INVENTION

Brivaracetam, with the chemical name of (S)-2-(R)-3-propylpyrrolidin-1-ylbutylamide, developed and produced by UCB Pharma, Belgium, is an analogue of antiepileptics levetiracetam pyrrolidine with the 4-carbon atom linked to n-propyl group. Brivaracetam is also a selective ligand with high affinity for brain synaptic vesicle protein 2A (SV2A). SV2A is an important site to inhibit partial epileptic seizures. The European Medicines Agency (EMA) and U.S. Food and Drug Administration (FDA) approved the use of brivaracetam, under trade name Briviact®, as an adjuvant drug for the treatment of patients aged 16 and above suffering from partial epilepsy seizures with or without secondary systemic seizures on Jan. 14, 2016 and Feb. 18, 2016, respectively.

Brivaracetam is a derivative of levetiracetam (Keppra®), which belongs to the third generation of antiepileptic drugs. It has high affinity for and can selectively bind to synaptic vesicle protein 2A (SV2A). SV2A is the site of action of antiepileptic drug (AED) levetiracetam. SV2A is located in the presynaptic membrane, which mediates the release of neurotransmitters and the vesicle recycling to maintain the normal functions of synaptic vesicles. The binding between AED and SV2A can reduce the release of excitatory neurotransmitters, and achieve the effect of controlling epileptic seizures by regulating the balance of excitatory transmitters and inhibitory transmitters in the brain. The affinity of brivaracetam is 15 to 30 times more than that of levetiracetam, which reduces the dosage by about 10 times. A small (n=29), open-label, prospective study shows that the living quality is improved while the control effect of epilepsy is not reduced in those patients who change from using levetiracetam to using brivaracetam due to behavioral adverse events.

At present, it is almost inevitable for current preparation processes of brivaracetam to separate its diastereoisomer (S)-2-(S)-3-propylpyrrolidon-1-ylbutylamide by chiral chromatographic columns. As mentioned in the original research patent document WO 2005028435, two diastereoisomers were separated by chromatography using chiral chromatographic columns with stationary phase and n-hexane/ethanol (45/55, V/V) as eluent at 25±2° C. Another synthesis route, described in patent document WO 2007065634, uses expensive metal catalyst RuCl$_3$. In this preparation method, it is also inevitably to separate brivaracetam (26%, e.e.=94%) from diastereoisomers thereof by column chromatography. Their structures are represented as follows:

RS configuration Brivaracetam     SS configuration Isomer

Patent document CN106748950A reports a method for preparing brivaracetam intermediate. The reaction route is as follows:

It uses R-phenylethylamine/isopropanol system to resolve the compound represented by B-IV to obtain the brivaracetam intermediate represented by B-VI The intermediate is used to prepare brivaracetam without resolution by chiral chromatographic columns, which can thus reduce the production cost. However, after repeating the examples in the literature, the inventors of the present application found that by using the R-phenylethylamine/isopropanol system, the effect of resolution and purification could not be achieved, and the brivaracetam intermediate represented by B-VI could not be obtained in high purity.

SUMMARY OF THE INVENTION

The purpose of this application is to provide a method for preparing the brivaracetam intermediate represented by B-R.

Furthermore, the application also provides a method for preparing brivaracetam in high purity by using the intermediate.

The first aspect of this application provides a method for preparing the brivaracetam intermediate represented by B-R, comprising the following steps:
(1) reacting the compound represented by B-P with 1S,2S-diphenylethylenediamine to obtain the compound represented by B-Q;
(2) converting the compound represented by B-Q to the brivaracetam intermediate represented by B-R;

In some embodiments of the first aspect of this application, step (1) comprises:
a. adding the compound represented by B-P and 1S,2S-diphenylethylenediamine to a resolution solvent, heating until it is dissolved and clarified, then cooling to crystallize, and separating to obtain a crude solid product of the compound represented by B-Q;
b. recrystallizing the crude solid product in a recrystallization solvent to obtain a refined product of the compound represented by B-Q.

In some embodiments of the first aspect of this application, the separating in step a can be achieved by filtering.

In some embodiments of the first aspect of this application, the molar ratio of the compound represented by B-P to 1S,2S-diphenylethylenediamine is 1:0.5-1.5, preferably 1:1.

In some embodiments of the first aspect of this application, the resolution solvent in step a can be at least one selected from the group consisting of methyl tertiary butyl ether, isopropyl ether, tetrahydrofuran (THF), acetonitrile, ethyl acetate, isopropyl acetate and ethylene glycol dimethyl ether, preferably at least one selected from the group consisting of isopropyl acetate, ethyl acetate, acetonitrile and ethylene glycol dimethyl ether.

In some embodiments of the first aspect of this application, the volume to mass ratio of the resolution solvent to the compound represented by B-P is 1-30 mL:1 g, preferably 1-10 mL:1 g, more preferably 3-6 mL:1 g.

In some embodiments of the first aspect of this application, in step a, heating is performed to a temperature of 25° C.-100° C. preferably 50° C.-75° C.

In some embodiments of the first aspect of this application, the recrystallization solvent in step b is at least one selected from the group consisting of methyl tertiary butyl ether, acetonitrile, ethyl acetate, isopropyl acetate and ethylene glycol dimethyl ether, preferably at least one selected from the group consisting of isopropyl acetate, acetonitrile, ethyl acetate and ethylene glycol dimethyl ether.

In some embodiments of the first aspect of this application, the volume to mass ratio of the recrystallization solvent to substrate, the compound represented by B-Q, is 1-10 mL:1 g. preferably 3 mL:1 g.

In some embodiments of the first aspect of this application, step (2) comprises:
c. converting the compound represented by B-Q to the brivaracetam intermediate represented by B-R in a reaction solvent comprising water in the presence of an acid.

In some embodiments of the first aspect of this application, the acid in step c is at least one of hydrochloric acid and trifluoroacetic acid.

In some embodiments of the first aspect of this application, the pH value of the reaction in step c is 1-2.

In some embodiments of the first aspect of this application, the reaction solvent in step c further comprises at least one of ethyl acetate and isopropyl acetate.

The second aspect of this application provides a method for preparing brivaracetam, which includes ammoniating the brivaracetam intermediate represented by B-R obtained by the above method to obtain brivaracetam.

In some embodiments of the second aspect of this application, the method for preparing brivaracetam comprises the following steps:
preparing the brivaracetam intermediate according to the above-mentioned method;
ammoniating the brivaracetam intermediate represented by B-R to obtain brivaracetam.

Advantageous Effect

In this application, the compound (2S)-2-(2-oxy-4-propylpyrrolidon-1-yl)butyric acid represented by B-P can be effectively resolved by using 1S,2S-diphenylethylenediamine as the resolution agent, so as to obtain the brivaracetam intermediate, (S)-2-((R)-2-oxy-4-propylpyrrolidon-1-yl)butyric acid represented by B-R.

Furthermore, the preparation of brivaracetam by utilizing this intermediate can omit the resolution step by chiral chromatographic columns, thus shortening the preparation time, simplifying the operation and reducing the cost.

BRIEF DESCRIPTION OF THE DRAWINGS

In order to illustrate the examples of the present application and the technical solutions of the prior art more clearly, the following description briefly introduces the drawings needed in the embodiments and the prior art. Obviously, the drawings in the following description are only some embodiments of the present application. For those skilled in the art, other drawings may also be obtained from these drawings without any creative efforts.

DETAILED DESCRIPTION OF THE INVENTION

Preparation of the Brivaracetam Intermediate

The synthesis route of the preparation method of the brivaracetam intermediate represented by B-R provided by this application is as follows:

step (1): reacting the compound represented by B-P with 1 S,2S-diphenylethylenediamine to obtain the compound represented by B-Q;

step (2): converting the compound represented by B-Q to the brivaracetam intermediate represented by B-R.

Through in-depth study of the prior art, the inventor of this application finds that some resolution agents reported in the prior art, such as R-phenylethylamine, can not resolve the compound represented by B-P. However, in the process of further exploration, the inventors unexpectedly found that the specific resolution agent 1S,2S-diphenylethylenediamine can effectively resolve the compound represented by B-P into the brivaracetam intermediate represented by B-R.

In some embodiments of this application, step (1) comprises.

a. adding the compound represented by B-P and 1S,2S-diphenylethylenediamine to the resolution solvent, heating until it is dissolved and clarified, then cooling to crystallize, and separating to obtain a crude solid product of the compound represented by B-Q;

b. recrystallizing the crude solid product in a recrystallization solvent to obtain a refined product of the compound represented by B-Q.

The inventors of the application further found that with the increase of the molar ratio of 1S,2S-diphenylethylenediamine to the compound represented by B-P, the yield of compound represented by B-Q increases firstly and then decreases; and when the chiral purity increases to a certain extent, it is basically unchanged. Considering the factors of yield, chiral purity and cost, the molar ratio of 1S,2S-diphenylethylenediamine to the compound represented by B-P should be controlled. In some embodiments of this application, the molar ratio of the compound represented by B-P to 1S,2S-diphenylethylenediamine is 1:0.5-1.5, preferably 1:1. Products with high yield and chiral purity can be obtained within such molar ratio range.

In some embodiments of this application, in step a, the resolution solvent can be at least one selected from the group consisting of methyl tertiary butyl ether, isopropyl ether, tetrahydrofuran, acetonitrile, ethyl acetate, isopropyl acetate and ethylene glycol dimethyl ether; preferably at least one selected from the group consisting of isopropyl acetate, ethyl acetate, acetonitrile and ethylene glycol dimethyl ether. The resolution solvents described above can be used alone, or more than two of these solvents can be used in combination in any proportion.

The inventors of the application further found that with the increase of the volume to mass ratio of the resolution solvent to the compound represented by B-P, the yield of the product, the compound represented by B-Q, decreases gradually while the chiral purity of the product increases. Considering the yield and chiral purity of the compound represented by B-Q, in some embodiments of this application, the volume to mass ratio of the resolution solvent to the compound represented by B-P is 1-30 mL:1 g, preferably 1-10 mL:1 g, and more preferably 3-6 mL:1 g. The compound represented by B-Q can be obtained in high yield and chiral purity within such volume to mass ratio range.

In some embodiments of this application, in step a, heating is performed to a temperature of 25° C.-100° C., preferably 50° C.-75° C.

In some embodiments of this application, the recrystallization solvent in step b is at least one selected from the group consisting of methyl tertiary butyl ether, acetonitrile, ethyl acetate, isopropyl acetate and ethylene glycol dimethyl ether. The recrystallization solvents described above can be used alone, or more than two of these solvents can be used in combination in any proportion. All of the refined products of the compound represented by B-Q obtained by using the above recrystallization solvent have high chiral purity. Especially, when at least one selected from the group consisting of isopropyl acetate, acetonitrile, ethyl acetate and ethylene glycol dimethyl ether is used as the recrystallization solvent, the chiral purity of the refined products of the compound represented by B-Q can reach 99% or more.

In some embodiments of this application, the volume to mass ratio of the recrystallization solvent to the crude solid product of the compound represented by B-Q is 1-30 mL:1 g, preferably 1-10 mL:1 g, more preferably 3 mL:1 g.

In some embodiments of this application, step (2) comprises:

c. converting the compound represented by B-Q to the brivaracetam intermediate represented by B-R in a reaction solvent comprising water in the presence of an acid.

The compound represented by B-Q can be resolved into the compound represented by B-R and a salt of the resolution agent by reacting with an acid. The compound represented by B-R is insoluble in water and soluble in organic solvents, while the salt of the resolution agent is soluble in water. Based on the difference in solubility, the compound represented by B-R can be separated with a reaction solvent comprising water.

The acid in step c is not specifically limited. For example, it can be at least one of hydrochloric acid and trifluoroacetic acid.

In some embodiments of this application, the pH value of the reaction in step c is 1-2. Adjusting the pH value of the reaction solvent to the above range by the acid can ensure the sufficient reaction of the compound represented by B-Q and improve the yield of the compound represented by B-R.

With regard to the reaction solvent, water can be used as the reaction solvent alone. When the compound represented by B-Q reacts with acid in water, the resulting salt of the resolution agent dissolves in water while the resulting compound represented by B-R precipitates out of water.

In some embodiments of this application, the reaction solvent can further comprise a certain amount of organic solvents, such as at least one of ethyl acetate and isopropyl acetate. The organic solvents can be used alone, or more than two of them can be used in combination in any proportion. In case that the reaction solvent contains both water and organic solvent, the compound represented by B-Q reacts with the acid in the reaction solvent, and the resulting salt of the resolution agent will enter into the aqueous phase; while the compounds represented by B-R will enter into the organic phase.

Further, w % ben the organic phase is separated from the aqueous phase, the organic phase can be extracted, concentrated and dried to obtain the brivaracetam intermediate represented by B-R.

Preparation of Brivaracetam

This application provides a method for preparing brivaracetam from the brivaracetam intermediate represented by B-R. Brivaracetam is obtained by ammoniating the brivaracetam intermediate represented by B-R. This method can avoid the use of chiral chromatographic columns, thus shortening the preparation time, simplifying the operation, and reducing the preparation cost.

In some embodiments of this application, the preparation method of brivaracetam comprises the following steps:

preparing the brivaracetam intermediate according to the above-mentioned method;
ammoniating the brivaracetam intermediate represented by B-R to obtain brivaracetam.

There is no specific restriction on the ammoniation of the brivaracetam intermediate represented by B-R. Known ammoniation reaction can be used to prepare brivaracetam. For example: brivaracetam can be obtained by reacting the brivaracetam intermediate represented by B-R with HATU (2-(7-Azabenzotriazol-1-yl)-N,N,N',N'-tetramethyluronium hexafluorophosphate), ammonium chloride and ethyldiisopropylamine in tetrahydrofuran, wherein the molar ratio of the brivaracetam intermediate, HATU, ammonium chloride and ethyldiisopropylamine thereinto is 1:1.5-2.5:2-3:2.5-3.5, preferably 1:2:2.5:3. The volume to mass ratio of tetrahydrofuran to the brivaracetam intermediate represented by B—R is 10-50 mL:1 g.

Brivaracetam can also be obtained by mixing the brivaracetam intermediate represented by B-R with dichloromethane, adding activator, and reacting with ammonia as introduced, wherein the activator can be at least one selected from the group consisting of thionyl chloride, oxalyl chloride, phosphorus oxychloride, methanesulfonyl chloride, trimethylacetyl chloride and isobutyl chlorocarbonate. The reaction temperature can be −20° C.-30° C.

The application will be further explained below in conjunction with specific embodiments.

In the following examples, the raw material (S)-2(4-propyl-1,5-dihydropyrrol-2-one)butyric acid can be prepared by known methods, such as by referring to the preparation method of example 1 in patent document CN107513031A, and other raw materials and reagents are commercially available.

Preparation of the Compound Represented by B-P

Example 1

150 g (S)-2(4-propyl-1,5-dihydropyrrol-2-one)butyric acid (0.71 mol) was added to a 2 L hydrogen autoclave, and then 1.5 L methanol and 1.5 g Pd(OH)$_2$/C (1%) were added to react for 20 hours under the pressure of 15-20 MPa. After filtration, the filtrate was concentrated and evaporated to remove methanol to obtain 140 g of the solid compound represented by B-P.

Figure 1:
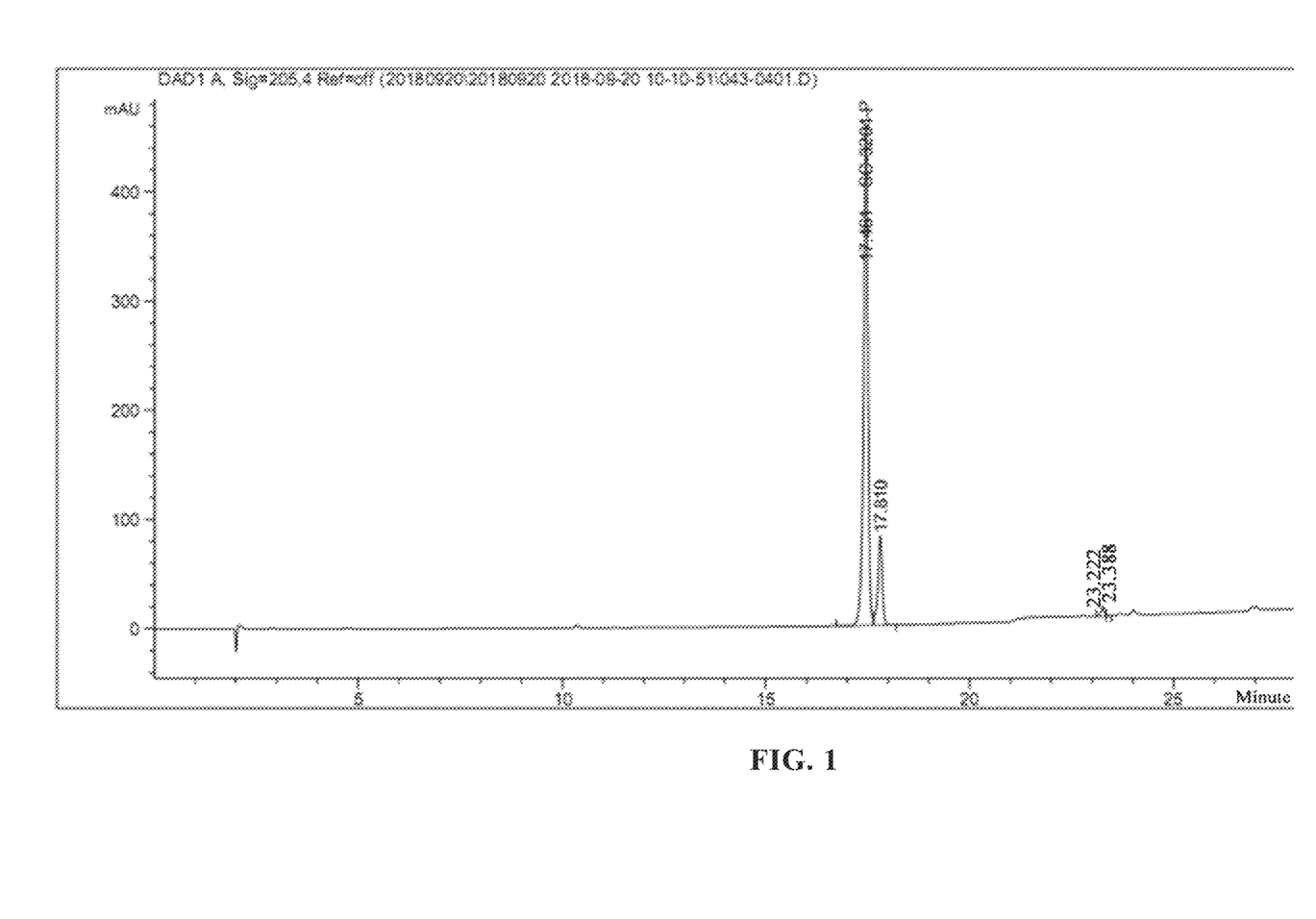
FIG. 1 is the liquid chromatogram of the compound represented by B-P prepared in Example 1.

According to the HPLC spectrum, the ratio of the two isomers in the compound represented by B-P was RS:SS=85:15, and the chiral purity was 85%, wherein RS was the isomerization product of RS configuration, i.e., the compound represented by B-R; SS was the isomerization product of SS configuration, i.e., the diastereoisomer of the compound represented by B-R. The HPLC chromatogram is shown in FIG. 1.

Example 2

150 g (S)-2(4-propyl-1,5-dihydropyrrol-2-one)butyric acid (0.71 mol) was added to a 2 L hydrogen autoclave, and then 1.5 L methanol and 45 g palladium on active charcoal (30%) were added to react for 20 hours under the pressure of 15-20 MPa. After filtration, the filtrate was concentrated and evaporated to remove methanol to obtain 145 g of solid compound represented by B-P.

Figure 2:
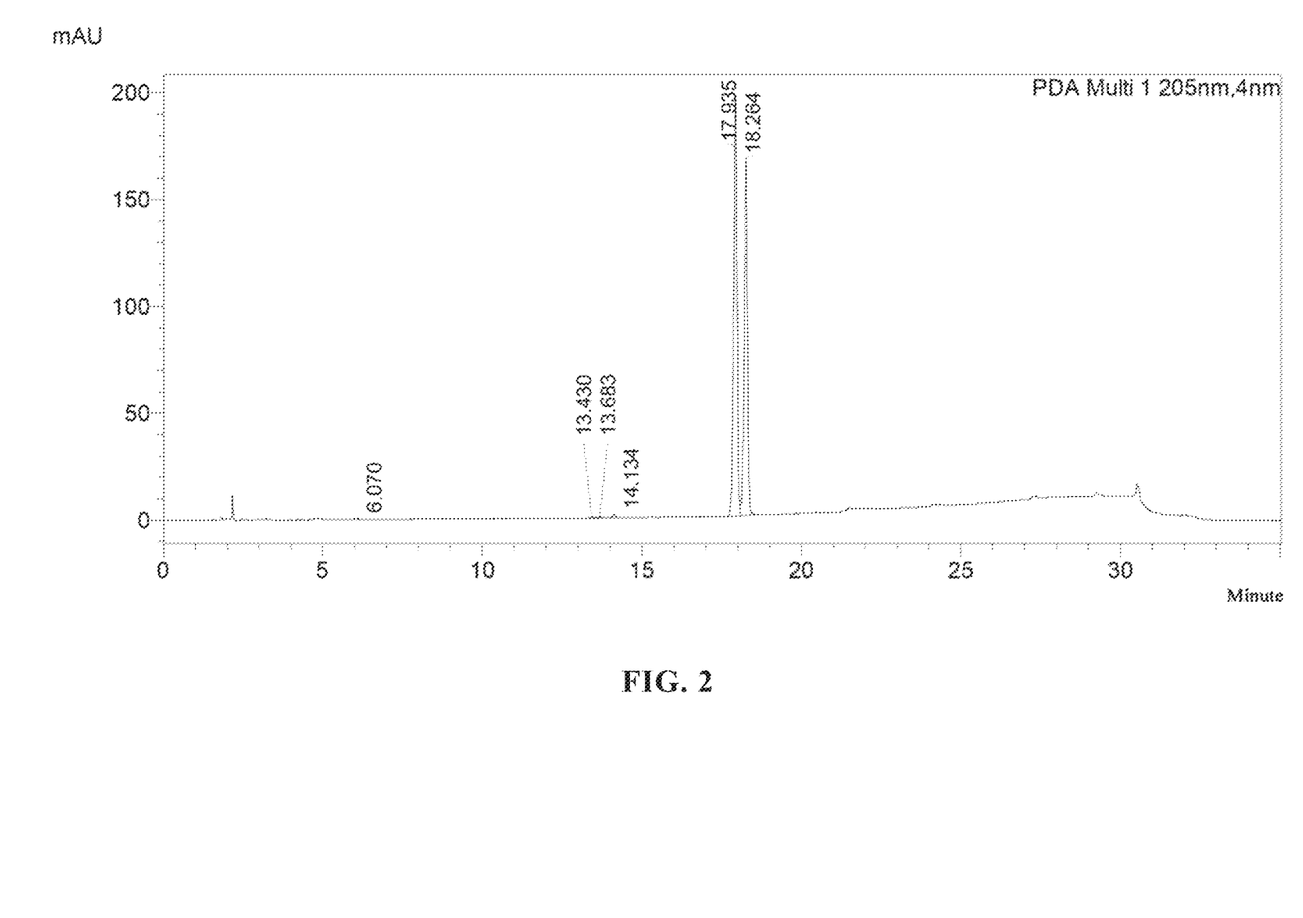
FIG. 2 is the liquid chromatogram of the compound represented by B-P prepared in Example 2.

According to the HPLC spectrum, the ratio of the two isomers in the compound represented by B-P was RS:SS=55:45, and the chiral purity was 55%, wherein RS was the isomerization product of RS configuration, i.e., the compound represented by B-R; and SS was the isomerization product of SS configuration, i.e., the diastereoisomer of the compound represented by B-P. The HPLC chromatogram is shown in FIG. 2.

Preparation of the Compound Represented by B-Q

Example 3

Figure 3:
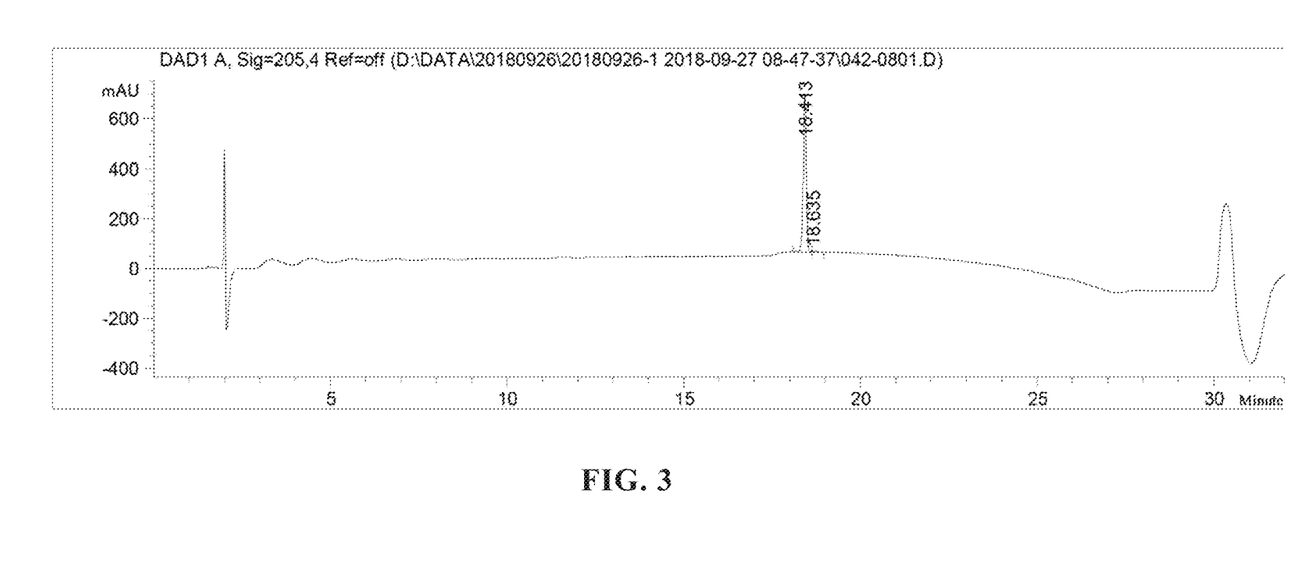
FIG. 3 is the liquid chromatogram of the compound represented by B-Q prepared in Example 3.

180 ml isopropyl acetate, 60 g of the compound represented by B-P prepared in Example 1 (0.28 mol, 1.0 eq, containing 15% of isomer) and 59.4 g 1S,2S-diphenylethylenediamine (1.0 eq. 0.28 mol) were added to a 500 ml three-necked flask, heated to about 72° C. until dissolved and clarified, naturally cooled to 20° C.±5° C., stirred for 1 hour, and then vacuum filtered to obtain 60 g of wet product. The wet product was then directly added to 180 ml isopropyl acetate, heated to 72° C. for dissolving, gradually cooled to 20° C. over 1.5 hours, and vacuum filtered to obtain 35.7 g of the compound represented by B-Q, yield: 30%. According to the HPLC spectrum, the chiral purity of the compound represented by B-Q was 99.8%, and the diastereoisomer was 0.2%. The HPLC diagram is shown in FIG. 3.

Example 4

540 ml isopropyl acetate, 60 g of the compound represented by B-P prepared in Example 1 (0.28 mol, 1.0 eq, containing 15% of isomer) and 59.4 g 1S,2S-diphenylethylenediamine (1.0 eq, 0.28 mol) were added to a 500 ml three-necked flask, heated to about 40° C., naturally cooled to 20° C.±5° C., stirred for 1 hour and then vacuum filtered to obtain 50 g of wet product. The wet product was then directly added to 180 ml isopropyl acetate, heated to 72° C. for dissolving, gradually cooled to 20° C. over 1.5 hours, and vacuum filtered to obtain 23.8 g of the compound represented by B-Q, yield: 20%; chiral purity: 99.8%; diastereoisomer 0.2%.

Example 5

180 ml isopropyl acetate, 60 g of the compound represented by B-P prepared in Example 1 (0.28 mol, 1.0 eq, containing 15% of isomer) and 59.4 g 1S,2S-diphenylethylenediamine (1.0 eq, 0.28 mol) were added to a 500 ml three-necked flask, heated to about 80° C. until dissolved and clarified, naturally cooled to 20° C.±5° C. stirred for 1 hour and then vacuum filtered to obtain 60 g of wet product. The wet product was then directly added to 180 ml isopropyl acetate, heated to 72° C. for dissolving, gradually cooled to 20° C. over 1.5 hours, and vacuum filtered to obtain 35 g of the compound represented by B-Q, yield: 29%; chiral purity: 99.8%; diastereoisomer 0.2%.

Example 6

180 ml isopropyl acetate, 60 g of the compound represented by B-P prepared in Example 1 (0.28 mol, 1.0 eq, containing 15% of isomer) and 29.7 g 1S,2S-diphenylethylenediamine (0.5 eq, 0.14 mol) were added to a 500 ml three-necked flask, heated to about 50° C. until dissolved and clarified, naturally cooled to 20° C.±5° C., stirred for 1 hour and then vacuum filtered to obtain 30 g of wet product. The wet product was then directly added to 90 ml isopropyl acetate, heated to 72° C. for dissolving, gradually cooled to 20° C. over 1.5 hours, and vacuum filtered to obtain 18 g of the compound represented by B-Q, yield: 15%; chiral purity: 99%; diastereoisomer 1.0%.

Example 7

180 ml isopropyl acetate, 60 g of the compound represented by B-P prepared in Example 1 (0.28 mol, 1.0 eq, containing 15% of isomer) and 90 g 1S,2S-diphenylethylenediamine (1.5 eq, 0.14 mol) were added to a 500 ml three-necked flask, heated to about 80° C. until dissolved and clarified, naturally cooled to 20° C.±5° C., stirred for 1 hour and then vacuum filtered to obtain 55 g of wet product. The wet product was then directly added to 180 ml isopropyl acetate, heated to 72° C. for dissolving, gradually cooled to 20° C. over 1.5 hours, and vacuum filtered to obtain 30 g of the compound represented by B-Q, yield: 25%; chiral purity: 99.8%, diastereoisomer 0.2%.

Example 8

180 ml isopropyl acetate, 60 g of the compound represented by B-P prepared in Example 2 (0.28 mol, 1.0 eq, containing 45% of isomer) and 59.4 g 1S,2S-diphenylethylenediamine (1.0 eq, 0.28 mol) were added to a 500 ml three-necked flask, heated to about 72° C. until dissolved and clarified, naturally cooled to 20° C.±5° C., stirred for 1 hour and then vacuum filtered to obtain 50 g of wet product. The wet product was then directly added to 180 ml isopropyl acetate, heated to 72° C. for dissolving, and then gradually cooled to 20° C. over 1.5 hours, and vacuum filtered to obtain 30 g of the compound represented by B-Q, yield: 25%; chiral purity: 98%.

Preparation of the Compound Represented by B-R

Example 9

30 g of the compound represented by B-Q prepared in Example 3, 120 ml water and 240 ml ethyl acetate were added to a 500 ml three-necked flask, in which the pH was adjusted to 1-2 with 6 N hydrochloric acid, stirred for 0.5 hours, and layered. The aqueous phase was extracted with 30 ml ethyl acetate. The organic phase was combined and concentrated under reduced pressure to obtain 15 g of white solid compound represented by B-R, with yield of 100% and the chiral purity of 98%. H-NMR data: 1H NMR (600 MHz, Chloroform-d) 4.64 (dd, J=10.8, 5.1 Hz, 1H), 3.43 (dd, J=9.4, 7.9 Hz, 1H), 3.18 (dd, J=9.4, 7.2 Hz, 1H), 2.60 (dd, J=16.8, 8.5 Hz, 1H), 2.34 (hept, J=7.7 Hz, 1H), 2.17 (dd, J=16.8, 8.3 Hz, 1H), 2.05 (dqd, J=14.8, 7.4, 5.0 Hz, 1H), 1.72 (ddq, J=14.5, 10.8, 7.3 Hz, 1H), 1.46 (t, J=7.5 Hz, 2H), 1.39-1.29 (m, 2H), 0.93 (td, J=7.4, 5.6 Hz, 6H).

Example 10

20 g of the compound represented by B-Q prepared in Example 4, 120 ml water and 240 ml ethyl acetate were added to a 500 ml three-necked flask, in which the pH was adjusted to 1-2 with 6 N trifluoroacetic acid, stirred for 0.5 hours, and layered. The aqueous phase was extracted with 30 ml isopropyl acetate. The organic phase was combined and concentrated under reduced pressure to obtain 10 g of white solid compound represented by B-R, with the yield of 100% and the chiral purity of 99.8%.

Preparation of Brivaracetam

Example 11

80 ml tetrahydrofuran, 6.4 g of the compound represented by B-R prepared in Example 9, 28.5 g HATU (0.075 mol), 4.9 g ammonium chloride (0.09 mol) and 11.7 g ethyldiisopropylamine (0.09 mol) were added to a 250 ml four-necked flask, and stirred for 2 hours at room temperature. 80 ml water and 160 ml ethyl acetate were added to the system under stirring, and then held until layered. The organic phase was washed once with each of 40 ml saturated sodium bicarbonate, 40 ml saturated ammonium chloride solution and 40 ml saturated sodium chloride solution. The organic phase was then dried with 5 g anhydrous sodium sulfate, filtered and concentrated to obtain 7 g of solid brivaracetam with HPLC purity of 99.5% and chiral purity of 99.85%.

Example 12 Effects of Resolution Solvents on Yield and Chiral Purity of the Compound Represented by B-Q 60 g (0.28 mol) of the compound represented by B-P and the resolution solvent were added to a reaction flask, and heated until the temperature was raised to 50° C. Then 0.28 mol of 1S,2S-diphenylethylenediamine was added, heated to about 70° C., cooled to 20° C. for crystallizing for 4 hours, and filtered to obtain the compound represented by B-Q. The effects of different solvents for resolution and different volume to mass ratios of the solvents for resolution to the compound represented by B-P on chiral purity and yield of the compound represented by B-Q are shown in Table 1:

TABLE 1

Effects of resolution solvents and different volume ratios

| Material specification | Resolution solvent | Volume to mass ratio (mL/g) | Compound represented by B-Q | Yield | Remark |
|---|---|---|---|---|---|
| Compound represented by B-P RS:SS = 85:15 | Ethyl acetate | 3:1 | 94:6 | 30% | Dissolved to clarified |
| | | 6:1 | 97:3 | 20% | Dissolved to clarified |
| | | 10:1 | 99:1 | 10% | Dissolved to clarified |
| | Isopropyl acetate | 3:1 | 98:2 | 40% | Dissolved to clarified |
| | | 6:1 | 98:2 | 30% | Dissolved to clarified |
| | | 10.1 | 99:1 | 10% | Dissolved to clarified |
| | Acetonitrile | 1:1 | 94:6 | 50% | Dissolved to clarified |
| | | 3:1 | 98:2 | 35% | Dissolved to clarified |
| | | 6:1 | 99:1 | 10% | Dissolved to clarified |
| | Ethylene glycol dimethyl ether | 1:1 | 91:9 | 45% | Dissolved to clarified |
| | | 3:1 | 94:6 | 25% | Dissolved to clarified |
| | | 6:1 | 96:4 | 20% | Dissolved to clarified |
| | | 10:1 | 97:3 | 10% | Dissolved to clarified |

Note:
(1) Dissolved to clarified means dissolved and clarified.

As can be seen from Table 1, ethyl acetate, isopropyl acetate, acetonitrile and ethylene glycol dimethyl ether all have resolution effects on the compound represented by B-P. With the increase of the volume to mass ratio of the resolution solvent to the compound represented by B-P, the yield of the compound represented by B-Q decreased gradually, while the chiral purity increased.

Example 13 Effects of the Recrystallization Solvents on Chiral Purity and Yield of Products The crude solid product of the compound represented by B-Q obtained by resolution was mixed with the recrystallization solvent, heated to 50° C., cooled to 20° C. for crystallizing for 4 hours, and filtered to obtain the refined products of the compound represented by B-Q. The effects of the types of the recrystallization solvent and the volume to mass ratio of the recrystallization solvent to the crude solid product of the compound represented by B-Q on crystallization efficiency are shown in Table 2:

TABLE 2

Effects of recrystallization solvents on crystallization efficiency

| Material specification | Recrystallization solvent | Volume to mass ratio (mL/g) | Chiral purity | Yield |
|---|---|---|---|---|
| Before the recrystallization of the compound represented by B-Q RS:SS = 95:5 | Ethylene glycol dimethyl ether | 3:1 | 99.5% | 30% |
| | Ethyl acetate | 3:1 | 99.8% | 49% |
| | Acetonitrile | 3.1 | 99.5% | 45% |
| | Isopropyl acetate | 3:1 | 99.8% | 40% |

As can be seen from Table 2: all of the chiral purity can reach more than 99% when using the four solvents including ethylene glycol dimethyl ether, ethyl acetate, acetonitrile, and isopropyl acetate for recrystallizing, in which the yield with ethyl acetate is the highest, which is 49%.

Comparative Example Resolution of the Compound Represented by B-P by R/S-Phenylethylamine The inventors of the present application repeated the example of resolution of the compound represented by B-P by R-phenylethylamine as mentioned in the patent document CN106748950A, which could not achieve the resolution effect. Further investigations on the effects of the resolution solvent on the resolution of the compound represented by B-P (RS:SS=55:45) by R/S-phenylethylamine are shown in Table 3:

TABLE 3

Investigation on the resolution solvent of R/S-phenylethylamine

| Resolution agent | Resolution solvent | Crystallization temperature | After resolution RS/SS | Yield |
|---|---|---|---|---|
| R-phenylethylamine | Isopropanol | 0~5° C. | 55/45 | 13% |
| R-phenylethylamine | Ethanol | (−20)~(−15)° C. | — | No solid precipitated |
| R-phenylethylamine | Isopropyl ether | (−20)~(−15)° C. | — | No solid precipitated |
| R-phenylethylamine | Tetrahydrofuran | (−20)~(−15)° C. | — | No solid precipitated |
| R-phenylethylamine | Methylbenzene | (−20)~(−15)° C. | — | No solid precipitated |
| R-phenylethylamine | Acetone | (−20)~(−15)° C. | — | No solid precipitated |
| R-phenylethylamine | Ethylene glycol dimethyl ether | (−20)~(−15)° C. | — | No solid precipitated |
| R-phenylethylamine | Methyl tertiary butyl ether | (−20)~(−15)° C. | — | No solid precipitated |
| R-phenylethylamine | Acetonitrile | (−20)~(−15)° C. | — | No solid precipitated |
| R-phenylethylamine | Ethyl acetate | 0~5° C. | 55/45 | 25% |
| R-phenylethylamine | Isopropyl acetate | (−20)~(−15)° C. | — | No solid precipitated |
| S-phenylethylamine | Isopropanol | 0~5° C. | 55/45 | 13% |
| S-phenylethylamine | Ethanol | (−20)~(−15)° C. | — | No solid precipitated |
| S-phenylethylamine | Isopropyl ether | (−20)~(−15)° C. | — | No solid precipitated |
| S-phenylethylamine | Tetrahydrofuran | (−20)~(−15)° C. | — | No solid precipitated |
| S-phenylethylamine | Methylbenzene | 0~5° C. | 55/45 | 25% |
| S-phenylethylamine | Acetone | (−20)~(−15)° C. | — | No solid precipitated |

TABLE 3-continued

Investigation on the resolution solvent of R/S-phenylethylamine

| Resolution agent | Resolution solvent | Crystallization temperature | After resolution RS/SS | Yield |
|---|---|---|---|---|
| S-phenyl-ethylamine | Ethylene glycol dimethyl ether | (−20)~(−15)° C. | — | No solid precipitated |
| S-phenyl-ethylamine | Methyl tertiary butyl ether | 0~5° C. | 55/45 | 36% |
| S-phenyl-ethylamine | Acetonitrile | 0~5° C. | 55/45 | 10% |
| S-phenyl-ethylamine | Ethyl acetate | 0~5° C. | 55/45 | 20% |
| S-phenyl-ethylamine | Isopropyl acetate | 0~5° C. | 57/43 | 35% |

It can be obtained from above Table 3 that the R/S-phenylethylamine recorded in patent document CN106748950A has no resolution effect on the compound represented by B-P.

The function of the above-mentioned examples is to explain the substantive content of the application, and it does not limit the protection scope of the application. A person of ordinary skill in the art should understand that the technical solution of the present application could be modified or equivalently replaced without departing from the essence and protection scope of the technical solution of the present application.

The invention claimed is:

1. A method for preparing a brivaracetam intermediate represented by B-R, comprising the following steps:

(1) reacting a compound represented by B-P with 1S,2S-diphenylethylenediamine to obtain a compound represented by B-Q; and (2) converting the compound represented by B-Q to the brivaracetam intermediate represented by B-R;

wherein step (1) comprising
  a. adding the compound represented by B-P and 1S,2S-diphenylethylenediamine to a resolution solvent, heating until it is dissolved and clarified, then cooling to crystallize, and separating to obtain a crude solid product of the compound represented by B-Q;
  b. recrystallizing the crude solid product in a recrystallization solvent to obtain a refined product of the compound represented by B-Q, and
  wherein the resolution solvent in step a is at least one selected from the group consisting of methyl tertiary butyl ether, isopropyl ether, tetrahydrofuran, acetonitrile, ethyl acetate, isopropyl acetate, and ethylene glycol dimethyl ether.

2. The method according to claim 1, wherein the molar ratio of the compound represented by B-P to 1S,2S-diphenylethylenediamine is 1:0.5-1.5.

3. The method according to claim 1, wherein the volume to mass ratio of the resolution solvent to the compound represented by B-P is 1-30 mL: 1 g.

4. The method according to claim 1, wherein in step a, heating is performed to a temperature of 25° C.-100° C.

5. The method according to claim 1, wherein in step b, the recrystallization solvent is at least one selected from the group consisting of methyl tertiary butyl ether, acetonitrile, ethyl acetate, isopropyl acetate, and ethylene glycol dimethyl ether.

6. The method according to claim 1, wherein the volume to mass ratio of the recrystallization solvent to the crude solid product of the compound represented by B-Q is 1-30 mL: 1 g.

7. The method according to claim 1, wherein step (2) comprises:
  c. converting the compound represented by B-Q to the brivaracetam intermediate represented by B-R in a reaction solvent comprising water in the presence of an acid.

8. The method according to claim 7, wherein the acid in step c is at least one of hydrochloric acid and trifluoroacetic acid.

9. The method according to claim 7, wherein the pH value of the reaction in step c is 1-2.

10. The method according to claim 7, wherein in step c, the reaction solvent further comprises at least one of ethyl acetate and isopropyl acetate.

11. A method for preparing brivaracetam, comprising the following steps:
  preparing the brivaracetam intermediate represented by B-R by using the method according to claim 1; and
  ammoniating the brivaracetam intermediate represented by B-R to obtain brivaracetam.

12. The method according to claim 2, wherein the molar ratio of the compound represented by B-P to 1S,2S-diphenylethylenediamine is 1:1.

13. The method according to claim 1, wherein the resolution solvent in step a is at least one selected from the group consisting of isopropyl acetate, ethyl acetate, acetonitrile, and ethylene glycol dimethyl ether.

14. The method according to claim 3, wherein the volume to mass ratio of the resolution solvent to the compound represented by B-P is 1-10 mL: 1 g.

15. The method according to claim 3, wherein the volume to mass ratio of the resolution solvent to the compound represented by B-P is 3-6 mL: 1 g.

16. The method according to claim 4, wherein in step a, heating is performed to a temperature of 50° C.-75° C.

17. The method according to claim 5, wherein in step b, the recrystallization solvent is at least one selected from the group consisting of isopropyl acetate, acetonitrile, ethyl acetate and ethylene glycol dimethyl ether.

18. The method according to claim 6, wherein the volume to mass ratio of the recrystallization solvent to the crude solid product of the compound represented by B-Q is 1-10 mL: 1 g.

\* \* \* \* \*